(12) United States Patent
Garcia Molina et al.

(10) Patent No.: US 10,328,234 B2
(45) Date of Patent: Jun. 25, 2019

(54) SYSTEM AND METHOD FOR ENHANCED KNOWLEDGE CONSOLIDATION BY SLEEP SLOW WAVE INDUCTION AND SENSORY CONTEXT RE-CREATION

(71) Applicants: KONINKLIJKE PHILIPS N.V., Eindhoven (NL); WISCONSIN ALUMNI RESEARCH FOUNDATION, Madison, WI (US)

(72) Inventors: Gary Nelson Garcia Molina, Madison, WI (US); Michele Bellesi, Madison, WI (US); Giulio Tononi, Verona, WI (US); Joanne Henriëtte Desirée Monique Westerink, Eindhoven (NL)

(73) Assignees: Koninklijke Philips N.V., Eindhoven (NL); Wisconsin Alumni Research Foundation, Madison, WI (US)

( * ) Notice: Subject to any disclaimer, the term of this patent is extended or adjusted under 35 U.S.C. 154(b) by 792 days.

(21) Appl. No.: 14/764,194

(22) PCT Filed: Jan. 8, 2014

(86) PCT No.: PCT/IB2014/058110
§ 371 (c)(1),
(2) Date: Jul. 29, 2015

(87) PCT Pub. No.: WO2014/118650
PCT Pub. Date: Aug. 7, 2014

(65) Prior Publication Data
US 2015/0374951 A1 Dec. 31, 2015

Related U.S. Application Data

(60) Provisional application No. 61/757,744, filed on Jan. 29, 2013.

(51) Int. Cl.
*A61M 21/02* (2006.01)
*A61B 5/0476* (2006.01)
(Continued)

(52) U.S. Cl.
CPC ............ *A61M 21/02* (2013.01); *A61B 5/0476* (2013.01); *A61B 5/4812* (2013.01); *A61M 21/00* (2013.01);
(Continued)

(58) Field of Classification Search
CPC ................. A61M 21/00; A61M 21/02; A61M 2021/0005; A61M 2021/0011;
(Continued)

(56) References Cited

U.S. PATENT DOCUMENTS

| 5,551,879 A | 9/1996 | Raynie et al. |
| 2006/0106275 A1 | 5/2006 | Raniere |

(Continued)

FOREIGN PATENT DOCUMENTS

| EP | 2524649 A2 | 11/2012 |
| WO | 2008039930 A2 | 4/2008 |

OTHER PUBLICATIONS

Massimini et al, "Triggering Sleep Slow Waves by Transcranial Magnetic Stimulation", PNAS, vol. 104, No. 20, 2007, pp. 8496-8501.
(Continued)

*Primary Examiner* — Carrie R Dorna (57) ABSTRACT

The present disclosure pertains to a system for enhancing knowledge consolidation in a subject during sleep. New declarative memories may be better consolidated by presenting sensory stimuli during slow wave sleep that correspond to sensory stimuli presented during prior wakeful learning. The sensory stimuli may include odors, sounds, visual stimulation, touches, tastes, and/or other types of
(Continued)

sensory stimuli. The system is configured to provide a prompt sensory stimulus during slow wave sleep that corresponds to a wakeful stimulus provided during wakeful learning. The prompt sensory stimulus may prompt enhanced knowledge consolidation in the subject. In some embodiments, the system may comprise one or more of a slow wave sleep inducer, a sensory stimulator, a sensor, a processor, electronic storage, a user interface, and/or other components.

21 Claims, 4 Drawing Sheets

(51) Int. Cl.
    *A61B 5/00*     (2006.01)
    *A61M 21/00*     (2006.01)

(52) U.S. Cl.
    CPC .... *A61B 5/6803* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2205/502* (2013.01); *A61M 2205/52* (2013.01)

(58) Field of Classification Search
    CPC .. A61M 2021/0016; A61M 2021/0022; A61M 2021/0027; A61M 2021/0044; A61M 2021/0055; A61M 2021/0066; A61M 2021/0072

See application file for complete search history.

(56) References Cited

U.S. PATENT DOCUMENTS

| | | | |
|---|---|---|---|
| 2008/0081941 A1* | 4/2008 | Tononi | A61N 2/006 600/14 |
| 2008/0234785 A1 | 9/2008 | Nakayama et al. | |
| 2011/0015469 A1 | 1/2011 | Walter et al. | |
| 2011/0200488 A1 | 8/2011 | Cennini et al. | |
| 2012/0251989 A1 | 10/2012 | Wetmore et al. | |

OTHER PUBLICATIONS

Tononi et al, "Enhancing Sleep Slow Waves With Natural Stimuli", Medicamundi, vol. 54, No. 2, 2010, pp. 82-88.
Rasch et al, "Odor Cues During Slow-Wave Sleep Prompt Declarative Memory Consolidation", Science, vol. 315, 2007, pp. 1-18.
Pearce, "A Model for Stimulus Generaliation in Pavlovian Conditioning", Psychological Review, vol. 94, No. 1, 1987, pp. 61-73.
Donohue et al, "Continuous Re-Exposure to Environmental Sound Cues During Sleep Does Not Improve Memory for Semantically Unrelated Word Pairs", Journal of Cognitive Education and Psychology, vol. 10, No. 2, 2011, pp. 167-177.

* cited by examiner

SYSTEM AND METHOD FOR ENHANCED KNOWLEDGE CONSOLIDATION BY SLEEP SLOW WAVE INDUCTION AND SENSORY CONTEXT RE-CREATION

CROSS-REFERENCE TO PRIOR APPLICATIONS

This application is the U.S. National Phase application under 35 U.S.C. § 371 of International Application Serial No. PCT/IB2014/058110, filed on Jan. 8, 2014, which claims the benefit of U.S. Application Ser. No. 61/757,744, filed on Jan. 29, 2013. These applications are hereby incorporated by reference herein.

The present disclosure pertains to a system for enhancing knowledge consolidation in a subject during sleep by slow wave induction and sensory context re-creation.

Knowledge acquisition may be enhanced via pharmaceutical therapies. Non-pharmaceutical therapies for enhancing knowledge acquisition are preferred over pharmaceutical therapies. Sensory stimulation during sleep is known. Sensory stimulation during sleep that mimics sensory stimulation during a wakeful period is known. Sensory stimulation during sleep is often applied continuously and/or at intervals that do not correspond to sleeping patterns of a subject. The present disclosure overcomes deficiencies in prior art systems.

Accordingly, one or more aspects of the present disclosure relate to a system for enhancing knowledge consolidation in a subject during sleep. The system comprises one or more slow wave sleep inducers, one or more sensory stimulators, and one or more processors. The one or more slow wave sleep inducers are configured to induce sleep slow waves in the subject. The one or more sensory stimulators are configured to provide sensory stimuli to the subject. The one or more processors are configured to execute computer program modules. The computer program modules comprise a sensory stimulus module, a slow wave sleep module, a timing module, and a control module. The sensory stimulus module is configured to obtain sensory stimulus parameters that define a prompt sensory stimulus to be provided to the subject. The slow wave sleep module is configured to control the one or more slow wave sleep inducers to induce slow wave sleep in the subject. The timing module is configured to determine a timing for delivery of the prompt sensory stimulus such that the prompt sensory stimulus will be provided to the subject during induced slow wave sleep. The control module is configured to control the one or more sensory stimulators to provide the prompt sensory stimulus to the subject according to the obtained sensory stimulus parameters at the timing determined by the timing module.

Yet another aspect of the present disclosure relates to a method for enhancing knowledge consolidation in a subject during sleep with a knowledge consolidation enhancement system. The knowledge consolidation enhancement system comprises one or more slow wave sleep inducers, one or more sensory stimulators, and one or more processors. The one or more processors are configured to execute computer program modules. The computer program modules comprise a sensory stimulus module, a slow wave sleep module, a timing module, and a control module. The method comprises obtaining sensory stimulus parameters that define a prompt sensory stimulus to be provided to the subject with the sensory stimulus module; controlling the one or more slow wave sleep inducers to induce slow wave sleep in the subject with the slow wave sleep module; determining a timing for delivery of the prompt sensory stimulus with the timing module such that the prompt sensory stimulus will be provided to the subject during induced slow wave sleep; and controlling the one or more sensory stimulators with the control module to provide the prompt sensory stimulus to the subject according to the obtained sensory stimulus parameters at the determined timing.

Still another aspect of present disclosure relates to a system for enhancing knowledge consolidation in a subject during sleep. The system comprises means for inducing slow wave sleep in the subject; means for providing sensory stimuli to the subject; means for obtaining sensory stimulus parameters that define a prompt sensory stimulus to be provided to the subject; means for controlling the means for inducing slow wave sleep in the subject; means for determining a timing for delivery of the prompt sensory stimulus such that the prompt sensory stimulus will be provided to the subject during induced slow wave sleep; and means for controlling the means for providing sensory stimuli to provide the prompt sensory stimulus to the subject according to the obtained sensory stimulus parameters at the determined timing.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Figure 1:
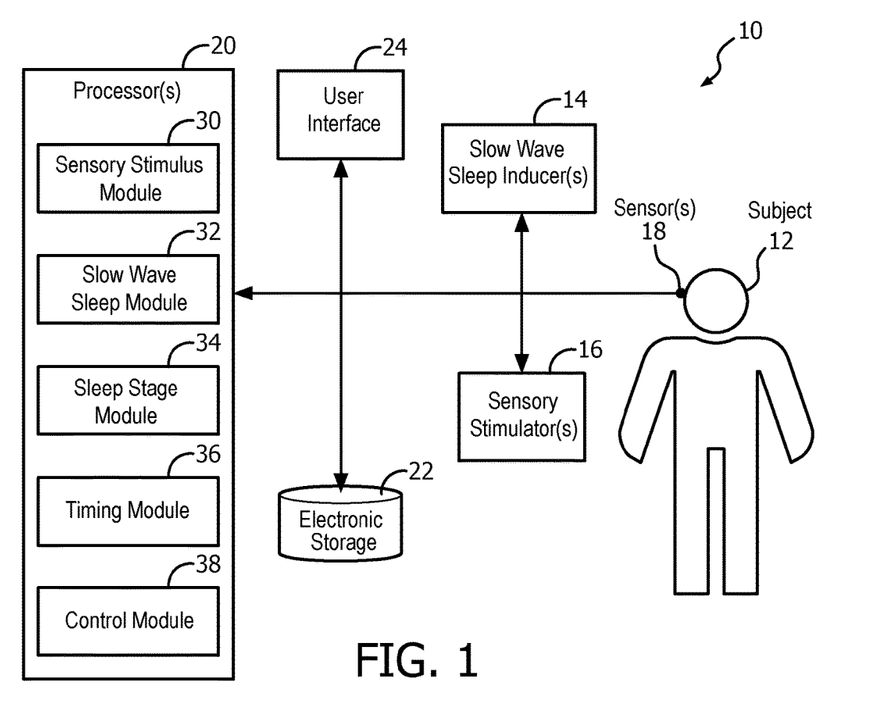
FIG. 1 is a schematic illustration of a system for enhancing knowledge consolidation in a subject during sleep.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 for enhancing knowledge consolidation in a subject 12 during sleep. New declarative memories may be better consolidated by presenting sensory stimuli during slow wave sleep that correspond to sensory stimuli presented during prior wakeful learning. In some embodiments, the sensory stimuli may be presented during slow wave sleep in the next sleep session (e.g., the night following the wakeful learning) of subject 12. The sensory stimuli may include different types of sensory stimuli. For example, the different types may include odors, sounds, visual stimulation (e.g., lights flashed on open and/or closed eyes), touches, tastes, and/or other types of sensory stimuli. Enhanced knowledge consolidation may result from providing a sensory stimulus during slow wave sleep that corresponds to a sensory stimulus presented during wakeful learning. System 10 is configured to provide a prompt sensory stimulus during slow wave sleep that corresponds to a wakeful sensory stimulus provided during wakeful learning. The prompt sensory stimulus and the wakeful sensory stimulus may include one or more sensory stimuli. The prompt sensory stimulus may prompt enhanced knowledge consolidation in subject 12. Sensory stimuli re-exposure may be ineffective during rapid eye movement (REM) sleep and/or wakefulness, and/or when the sensory stimuli had been omitted during prior learning. In some embodiments, system 10 may comprise one or more of a slow wave sleep inducer 14, a sensory stimulator 16, a sensor 18, a processor 20, electronic storage 22, a user interface 24, and/or other components.

Figure 2:
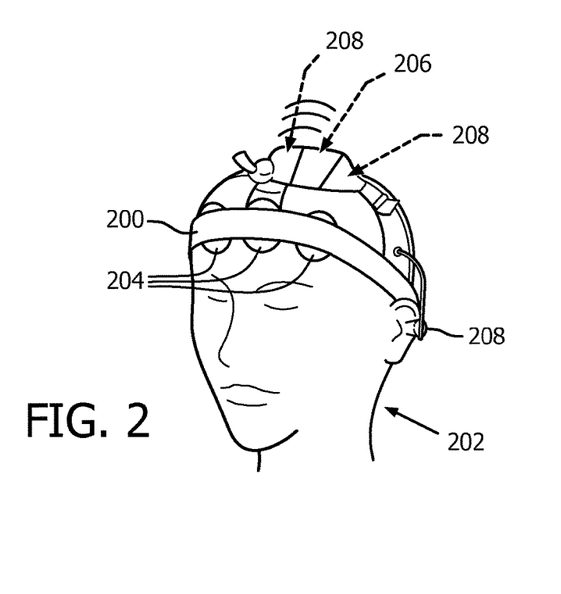
FIG. 2 illustrates a headset worn by a subject and includes sensing electrodes, a bio-signal amplifier, and a wireless audio device.

In FIG. 1, slow wave sleep inducer 14, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 2 illustrates a headset 200 worn by a subject 202 and includes sensing electrodes 204, a bio-signal amplifier 206, and a wireless audio device 208. Sensing electrodes 204 and bio-signal amplifier 206 may be represented, for example, by sensor 18 in FIG. 1. Wireless audio device 208 may be represented, for example, by slow wave sleep inducer 14 and/or sensory stimulator 16 shown in FIG. 1.

Returning to FIG. 1, slow wave sleep inducer 14 is configured to induce slow wave sleep in subject 12. In some embodiments, slow wave sleep inducer 14 may be configured to induce slow wave sleep through non-invasive brain stimulation and/or other methods. Slow wave sleep inducer 14 may be configured to induce slow wave sleep through non-invasive brain stimulation using slow wave sleep induction stimuli. Similar to the sensory stimuli presented during slow wave sleep to enhance knowledge consolidation, the slow wave sleep induction stimuli include odors, sounds, visual stimulation, touches, tastes, and/or other stimuli. The slow wave sleep induction stimuli should not re-create the sensory context created during wakeful learning. For example, transcranial magnetic stimulation may be applied to subject 12 to trigger slow wave sleep. As another example, slow wave sleep inducer 14 may be configured to induce slow wave sleep via auditory stimulation of subject 12. Examples of slow wave sleep inducer 14 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, and/or other devices.

Sensory stimulator 16 is configured to provide sensory stimuli to subject 12. Sensory stimulator 16 is configured to provide sensory stimuli to subject 12 during slow wave sleep, and/or at other times. In some embodiments, sensory stimulator 16 is configured to provide sensory stimuli to subject 12 during a period of wakeful learning of subject 12. The period of wakeful learning may occur prior to the slow wave sleep. In some embodiments, sensory stimulator 16 may include devices configured to generate odors, sounds, visual stimulation, touches, tastes, and/or other sensory stimuli. Sensory stimulator 16 may be configured to generate and/or provide one or more sensory stimuli to create a sensory context during slow wave sleep, during wakeful learning, and/or at other times. For example, sensory stimulator 16 may be configured to provide an odor to subject 12 during wakeful learning and again during slow wave sleep. In some embodiments, sensory stimulator 16 may include slow wave sleep inducer 14. Examples of sensory stimulator 16 may include light generators, a fragrance dispenser, a music player, a tone generator, a vibratory stimuli generator, and/or other devices.

Sensor 18 is configured to generate output signals conveying information related to a current sleep stage of the subject. The current sleep stage of the subject may correspond to one or more of non-rapid eye movement (NREM) stage N1, stage N2, or stage N3 sleep, and/or rapid eye movement (REM) sleep. In some embodiments, NREM stage 3 or stage 2 sleep may be slow wave sleep. Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to a current sleep stage of the subject indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location in communication with subject 12, this is not intended to be limiting. Sensor 18 may include sensors disposed in a plurality of locations, such as for example, within (or in communication with) slow wave sleep inducer 14, within (or in communication with) sensory stimulator 16, and/or in other locations.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., slow wave sleep inducer 14), or processor 20 may represent processing functionality of a plurality of devices operating in coordination.

As shown in FIG. 1, processor 20 is configured to execute one or more computer program modules. The one or more computer program modules may comprise one or more of a sensory stimulus module 30, a slow wave sleep module 32, a sleep stage module 34, a timing module 36, a control module 38, and/or other modules. Processor 20 may be configured to execute modules 30, 32, 34, 36, and/or 38 by software; hardware; firmware; some combination of software, hardware, and/or firmware; and/or other mechanisms for configuring processing capabilities on processor 20.

It should be appreciated that although modules 30, 32, 34, 36, and 38 are illustrated in FIG. 1 as being co-located within a single processing unit, in implementations in which processor 20 comprises multiple processing units, one or more of modules 30, 32, 34, 36, and/or 38 may be located remotely from the other modules. The description of the functionality provided by the different modules 30, 32, 34, 36, and/or 38 described below is for illustrative purposes, and is not intended to be limiting, as any of modules 30, 32, 34, 36, and/or 38 may provide more or less functionality than is described. For example, one or more of modules 30, 32, 34, 36, and/or 38 may be eliminated, and some or all of its functionality may be provided by other modules 30, 32, 34, 36, and/or 38. As another example, processor 20 may be configured to execute one or more additional modules that may perform some or all of the functionality attributed below to one of modules 30, 32, 34, 36, and/or 38.

Sensory stimulus module 30 is configured to obtain sensory stimulus parameters that define the prompt sensory stimulus to be provided to subject 12. The prompt sensory stimulus is provided to subject 12 during induced slow wave sleep. The prompt sensory stimulus may facilitate knowledge consolidation in subject 12. The sensory stimulus parameters that define the prompt sensory stimulus may include the type of sensory stimulus (e.g., odor, sound, touch, visual, taste), a duration, an intensity (e.g., a strong odor), a frequency, a duty cycle, timing, and/or other parameters. In some embodiments, sensory stimulus module 30 is configured to obtain the sensory stimulus parameters that define the prompt sensory stimulus based on the wakeful sensory stimulus provided to subject 12 during a period of wakeful learning by subject 12. In some embodiments, sensory stimulus module 30 may obtain (using incorporated sensors) the sensory stimulus parameters present (not necessarily provided) during the period of wakeful learning such that the obtained present sensory stimulation parameters may be reproduced during slow wave sleep. In some embodiments, the period of wakeful learning is a period of time during which subject 12 learns specific information. Learning specific information may include, for example, studying test notes for a test, reading a book, and/or other learning activities. In some embodiments, the material to be learned may be presented by system 10 (e.g., via user interface 24), and/or in other ways. For example, the specific information to be learned may be presented to subject 12 in a variety of forms including on a display screen of user interface 24, on a display screen of a computing device (e.g., a desktop computer, a laptop computer, a tablet computer, a smartphone), in printed form, in the form of audio content, and/or in other forms.

Slow wave sleep module 32 is configured to control slow wave sleep inducer 14 to induce slow wave sleep in subject 12. In some embodiments, slow wave sleep module 32 may be configured to control slow wave sleep inducer 14 to induce slow-wave sleep through non-invasive brain stimulation, and/or other stimulation. Controlling slow wave sleep inducer 14 to induce slow wave sleep through non-invasive brain stimulation may include controlling slow wave sleep inducer 14 to provide the slow wave sleep induction stimuli. For example, slow wave sleep module 32 may control slow wave sleep inducer 14 to induce slow wave sleep via transcranial magnetic stimulation. As another example, slow wave sleep module 32 may control slow wave sleep inducer 14 to induce slow way sleep via auditory stimulation of subject 12.

Figure 3:
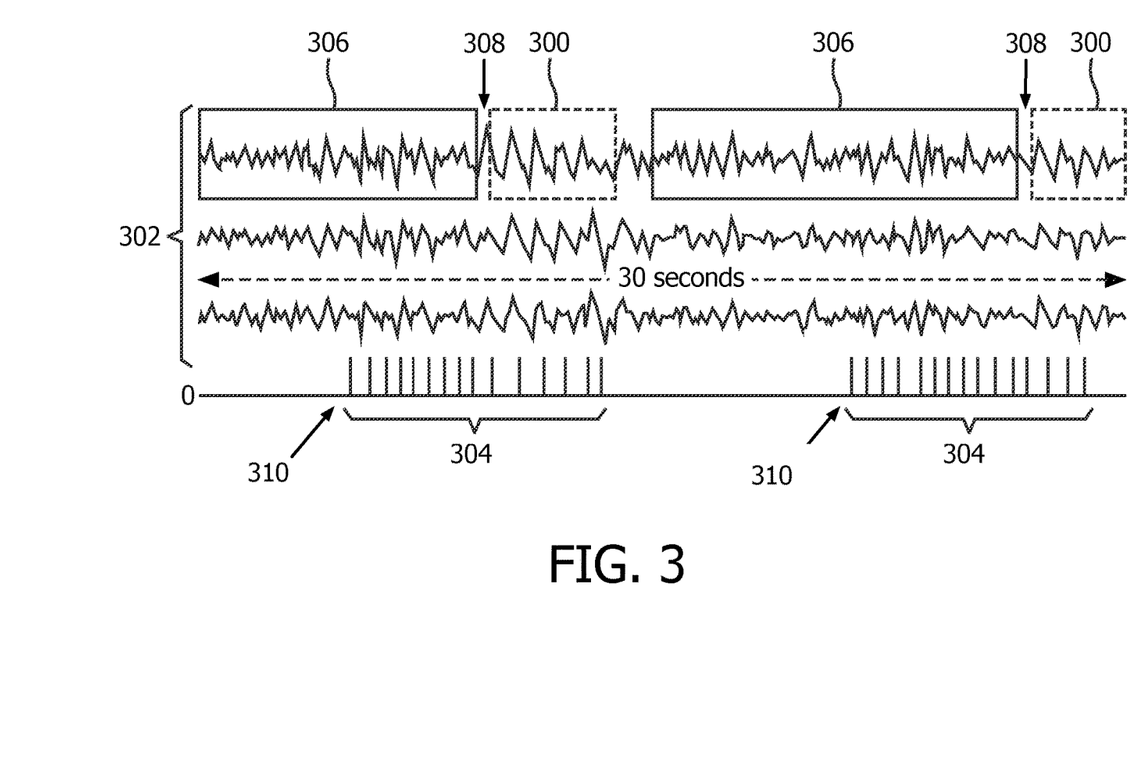
FIG. 3 illustrates two induced slow wave sleep cycles in a view of an EEG.

In some embodiments, slow wave sleep may be observed by way of an electroencephalogram (EEG). By way of a non-limiting example, FIG. 3 illustrates two induced slow wave sleep cycles 300 in a view 302 of an EEG. In the example shown in FIG. 3, slow wave sleep was induced with auditory tones. The timing of the auditory tones is represented by vertical bars 304. Non-slow wave sleep 306 transitions to slow wave sleep 300 at a time point 308 after the start 310 of the audio tones.

Returning to FIG. 1, sleep stage module 34 is configured to identify slow wave sleep in subject 12. Sleep stage module 34 is configured to identify slow wave sleep in subject 12 based on the output signals from sensors 18, and/or based on other information. In some embodiments, sleep stage module 34 may identify slow wave sleep in subject 12 based on an analysis of the information conveyed by the output signals. The analysis may include generating and/or monitoring an EEG during a sleep session of subject 12. In some embodiments, the analysis may include detecting slow wave sleep based on a slow wave sleep ratio. In some embodiments, the ratio may be:

$$\rho = \log\left(\frac{\beta}{\delta}\right),$$

where $\beta$ and $\delta$ represent a power in a beta band (e.g., usually defined as the power in the frequency range 15-30 Hz although variations in limits of the range are very common) of the EEG and a delta band (usually defined as the power in the frequency range 0.5-4.5 Hz although, just as in the case of the beta band, there is no standard definition of the frequency limits) of the EEG respectively. In some embodiments, sleep stage module 34 is configured to identify slow wave sleep in subject 12 responsive to an instantaneous slow wave sleep ratio $\rho(t)$, estimated based on instantaneous powers $\beta(t)$ and $\delta(t)$, staying below a threshold ratio for longer than a given period of time. In some embodiments, the threshold ratio and/or the given period of time may be determined based on previous sleep sessions of subject 12, and/or other information. In some embodiments, the threshold ratio and/or the given period of time may be programmed at manufacture. For example, the threshold ratio and/or the given period of time may be programmed at manufacture based on empirically accepted values such as a threshold ratio of about −2, and/or a given period of time of about 2 minutes. In some embodiments, system 10 may count the number of slow waves because these are identifiable from the EEG and have typical amplitude and durations. The amplitude and duration may be used to program an algorithm to automatically detect such slow waves.

In some embodiments, sleep stage module 34 may be configured to identify sleep stages in addition to, and/or instead of slow wave sleep. In some embodiments, slow wave sleep module 32 may be configured to control slow wave sleep inducer 14 to induce slow wave sleep in subject 12 responsive to sleep stage module 34 identifying a specific sleep stage (e.g., N1, N2, N3) while subject 12 is sleeping.

For example, slow wave sleep module 32 may be configured to control slow wave sleep inducer 14 to induce slow wave sleep in subject 12 responsive to sleep stage module 34 identifying sleep stage N2 while subject 12 is sleeping. Slow wave sleep module 32 may be configured to control slow wave sleep inducer 14 to induce slow wave sleep in subject 12 responsive to sleep stage module 34 identifying a specific sleep stage because the likelihood for slow-wave induction during the specific sleep stage may be comparatively higher than in other sleep stages, and/or an arousal threshold (e.g., the user is less likely to be awakened by sensory stimuli) may be higher during the specific sleep stage.

Timing module 36 is configured to determine timing for delivery of the prompt sensory stimulus. Timing module 36 is configured to determine timing for delivery of the prompt sensory stimulus such that the prompt sensory stimulus is provided to subject 12 during induced slow wave sleep. In some embodiments, timing module 36 is configured to determine the timing for delivery of the prompt sensory stimulus based on identification of slow wave sleep in subject 12 by sleep stage module 34. For example, timing module 36 may determine the timing for delivery of the prompt sensory stimulus such that delivery of the prompt sensory stimulus coincides with the start of slow wave sleep and/or stops with the end of slow wave sleep.

Figure 4:
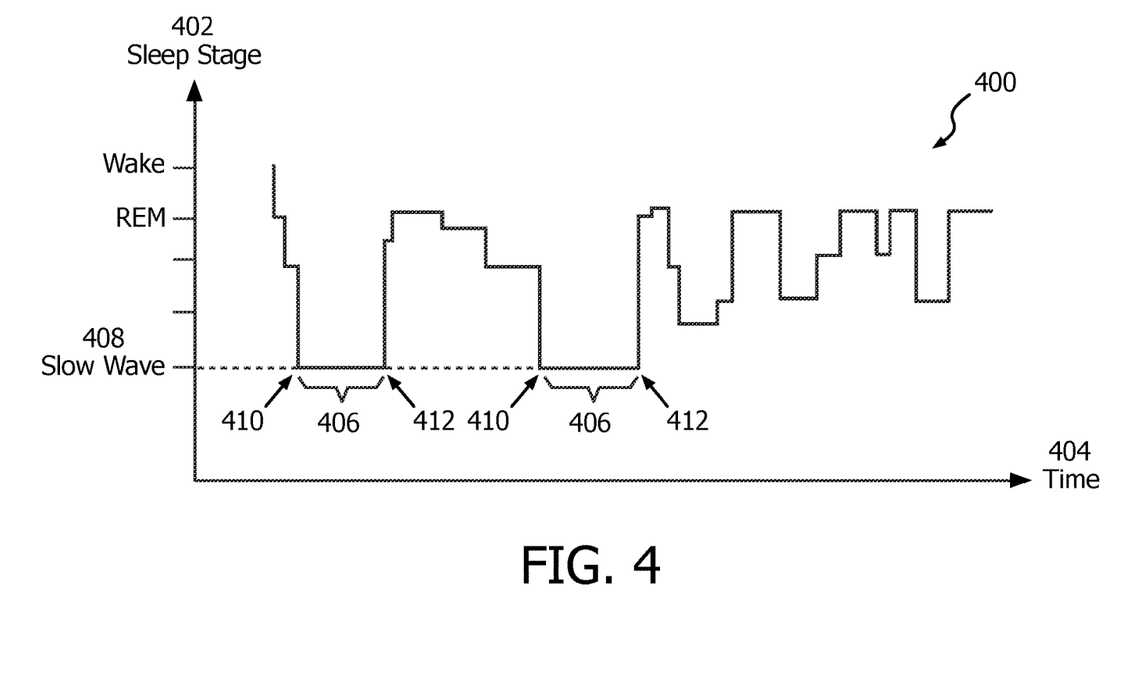
FIG. 4 illustrates an example of a hypnogram.

FIG. 4 illustrates an example of a hypnogram 400. Hypnogram 400 illustrates sleep stage 402 variation over time 404 for a sleep session of a subject. In the example shown in FIG. 4, the prompt sensory stimulus is timed 406 for delivery during periods of slow wave sleep 408. In some embodiments, slow waves may not be present throughout the whole N3 period, for example, but it may be significantly more likely that such slow waves are present during N3. Slow waves may also be present (although to a lesser extent) during N2, for example. Delivery of the prompt sensory stimulus is timed 406 such that the delivery of the prompt sensory stimulus starts with the start 410 of slow wave sleep and/or stops with the end 412 of slow wave sleep.

Returning to FIG. 1, in some embodiments, timing module 36 is configured to determine the timing for delivery of the prompt sensory stimulus based on a timing of the start of slow wave sleep induction by slow wave sleep module 32. In some embodiments, timing module 36 is configured to determine timing for delivery of the prompt sensory stimulus such that the prompt sensory stimulus is provided to subject 12 beginning at the start time of slow wave sleep induction. In some embodiments, timing module 36 is configured to determine timing for delivery of the prompt sensory stimulus such that the prompt sensory stimulus is provided to subject 12 beginning at one or more predetermined amounts of time after the start time of slow wave sleep induction by slow wave sleep module 32. In some embodiments, the one or more predetermined amounts of time may be based on typical amounts of time between the beginning of slow wave sleep induction and the beginning of slow wave sleep in subject 12 and/or in other subjects. The typical amounts of time may be determined based on a current sleep session of subject 12, previous sleep sessions of subject 12, and/or other sleep sessions. In some embodiments, the one or more predetermined amounts of time may be programmed at manufacture, set by a user via user interface 24, and/or determined by other methods. In some embodiments, the basis (e.g., based on identification of slow wave sleep, based on the start time of slow wave sleep induction) for determining the timing of the prompt sensory stimulus may be programmed at manufacture, set by a user via user interface 24, and/or determined by other methods.

Control module 38 is configured to control sensory stimulator 16 to provide the prompt sensory stimulus to subject 12. Control module 38 is configured to control sensory stimulator 16 to provide the prompt sensory stimulus according to the obtained sensory stimulus parameters at the timing determined by timing module 36. Control module 38 is configured to control sensory stimulator 16 to provide the prompt sensory stimulus to subject 12 such that the prompt sensory stimulus corresponds to the wakeful sensory stimulus provided during the period of wakeful learning. For example, control module 38 may control sensory stimulator 16 to provide a lavender fragrance to subject 12 at the timing determined by timing module 36. The lavender fragrance may have the same intensity as a lavender fragrance provided to subject 12 during a period of wakeful learning.

In some embodiments, control module 38 is configured to control sensory stimulator 16 to provide the wakeful sensory stimulus during the period of wakeful learning by subject 12. In some embodiments, during the period of wakeful learning, control module 38 may control sensory stimulator 16 and/or other devices to provide the wakeful sensory stimulus such that sensory stimuli of the wakeful sensory stimulus do not interfere with the ability of subject 12 to process the material to be learned. For example, control module 38 may control sensory stimulator 16 to provide the wakeful sensory stimulus at a low intensity level.

In some embodiments, control module 38 may be configured to control sensory stimulator 16 to provide the wakeful sensory stimulus via types of stimuli that engage senses not involved in the learning process. For example, control module 38 may be configured to control sensory stimulator 16 to provide olfactory stimuli while subject 12 learns printed material. Control module 38 may be configured to control sensory stimulator 16 to provide auditory stimuli (e.g., music) during a visual learning task.

In some embodiments, control module 38 may be configured such that controlling sensory stimulator 16 to provide a prompt sensory stimulus that corresponds to the wakeful sensory stimulus includes controlling sensory stimulator 16 to provide an exact match between the prompt sensory stimulus and the wakeful sensory stimulus, and/or controlling sensory stimulator 16 to provide a prompt sensory stimulus that is similar to the wakeful sensory stimulus. In some embodiments, differences between the prompt sensory stimulus and the wakeful sensory stimulus may enhance an environment for sleeping without interrupting knowledge consolidation. For example, differences between the prompt sensory stimulus and the wakeful sensory stimulus may include lower environmental light intensity and/or no light (e.g., darkness at night) during sleep. As another example, a prompt sensory stimulus may include a lavender scent to enhance sleep that was not included in the wakeful sensory stimulus during learning.

In some embodiments, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of slow wave sleep inducer 14, sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with slow wave sleep inducer 14, sensory stimulator 16, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 5:
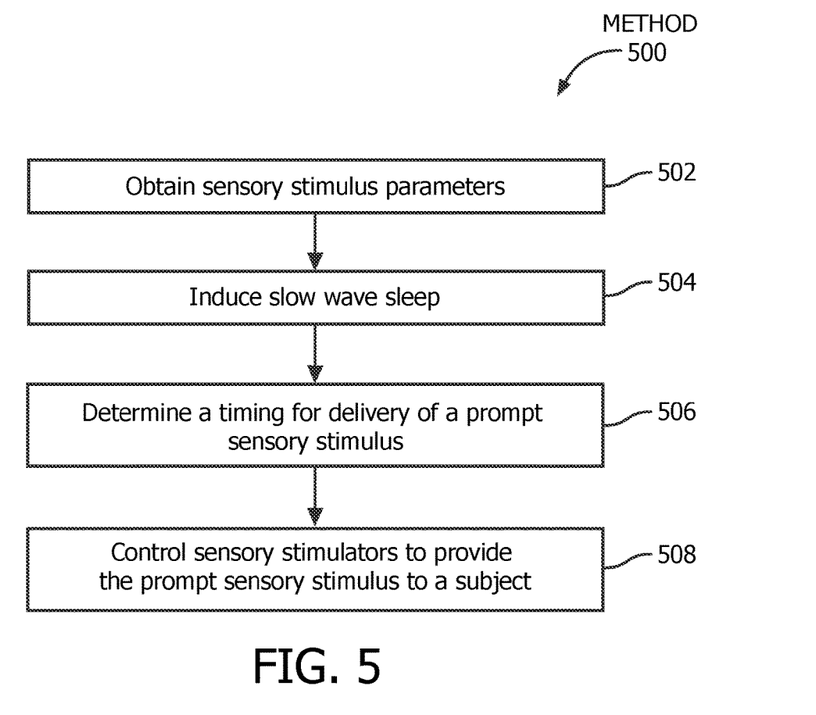
FIG. 5 illustrates a method for enhancing knowledge consolidation in a subject during sleep with a knowledge consolidation enhancement system.

FIG. 5 illustrates a method 500 for enhancing knowledge consolidation in a subject during sleep with a knowledge consolidation enhancement system. The knowledge consolidation enhancement system comprises one or more slow wave sleep inducers, one or more sensory stimulators, and one or more processors. The one or more processors are configured to execute computer program modules. The computer program modules comprise a sensory stimulus module, a slow wave sleep module, a timing module, and a control module. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, sensory stimulus parameters are obtained. The sensory stimulus parameters define a prompt sensory stimulus to be provided to the subject. The sensory stimulus parameters that define the prompt sensory stimulus are obtained based on a wakeful sensory stimulus provided to the subject during a period of wakeful learning by the subject. In some embodiments, operation 502 is performed by a computer program module the same as or similar to sensory stimulus module 30 (shown in FIG. 1 and described herein).

At an operation 504, slow wave sleep is induced in the subject. Slow wave sleep is induced in the subject by controlling the one or more slow wave sleep inducers to induce slow wave sleep in the subject. In some embodiments, operation 504 is performed by a computer program module the same as or similar to slow wave sleep module 32 (shown in FIG. 1 and described herein).

At an operation 506, a timing for delivery of the prompt sensory stimulus is determined. The timing for delivery of the prompt sensory stimulus is determined such that the prompt sensory stimulus is provided to the subject during induced slow wave sleep. In some embodiments, operation 506 is performed by a computer program module the same as or similar to timing module 36 (shown in FIG. 1 and described herein).

At an operation 508, the one or more sensory stimulators are controlled to provide the prompt sensory stimulus to the subject. The one or more sensory stimulators are controlled to provide the prompt sensory stimulus to the subject according to the obtained sensory stimulus parameters at the determined timing. The one or more sensory stimulators are controlled to provide the prompt sensory stimulus to the subject such that the prompt sensory stimulus corresponds to the wakeful sensory stimulus provided during the period of wakeful learning. In some embodiments, operation 508 is performed by a computer program module the same as or similar to control module 38 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system for enhancing knowledge consolidation in a subject during sleep, the system comprising:
   one or more slow wave sleep inducers configured to induce slow wave sleep in the subject;
   one or more sensory stimulators configured to provide sensory stimuli to the subject; and
   one or more computer processors configured by computer readable instructions to execute computer program modules, the computer program modules comprising:
      a sensory stimulus module configured to obtain sensory stimulus parameters that define a prompt sensory stimulus to be provided to the subject, the prompt sensory stimulus comprising a first type of sensory stimulus, the first type of sensory stimulus configured to recreate a learning context corresponding to a period of wakeful learning by the subject;
      a slow wave sleep module configured to control the one or more slow wave sleep inducers to induce slow wave sleep in the subject by providing a second type of sensory stimulus to the subject, the second type of sensory stimulus being different than the first type of sensory stimulus such that the second type of sensory stimulus does not recreate the learning context corresponding to the period of wakeful learning by the subject;
      a timing module configured to determine a timing with respect to the control of the one or more slow wave sleep inducers for delivery of the prompt sensory stimulus such that the prompt sensory stimulus will be provided to the subject during induced slow wave sleep; and
      a control module configured to, responsive to the slow wave sleep being induced, control the one or more sensory stimulators to provide the prompt sensory stimulus to the subject according to the obtained sensory stimulus parameters at the timing determined by the timing module;
      wherein the timing module is configured to determine the timing for delivery of the prompt sensory stimulus such that delivery of the prompt sensory stimulus begins a predetermined amount of time after the start of slow wave sleep induction.

2. The system of claim 1, further comprising one or more sensors configured to generate output signals conveying information related to a current sleep stage of the subject.

3. The system of claim 2, wherein the computer program modules further comprise a sleep stage module configured to identify non-rapid eye movement (NREM) sleep in the subject based on the output signals; and
   wherein the timing module is further configured to determine the timing for delivery of the prompt sensory stimulus based on identification of NREM sleep in the subject by the sleep stage module.

4. The system of claim 1, wherein the sensory stimulus module is further configured to obtain the sensory stimulus parameters that define the prompt sensory stimulus based on a wakeful sensory stimulus provided to the subject during the period of wakeful learning by the subject.

5. The system of claim 4, wherein the control module is further configured to control the one or more sensory stimulators to provide the prompt sensory stimulus to the subject such that the prompt sensory stimulus corresponds to the wakeful sensory stimulus provided during the period of wakeful learning.

6. The system of claim of claim 4, wherein the sensory stimulus module is configured such that the sensory stimulus parameters that define the prompt sensory stimulus include the first type of sensory stimulus, a duration, an intensity, a frequency, and a duty cycle of the prompt sensory stimulus.

7. The system of claim 1, wherein the timing module is configured such that the predetermined amount of time after the start of slow wave sleep induction is determined based on a typical amount of time between the start of slow wave sleep induction and the start of slow wave sleep in the subject.

8. A method for enhancing knowledge consolidation in a subject during sleep with a knowledge consolidation enhancement system, the knowledge consolidation enhancement system comprising one or more slow wave sleep inducers, one or more sensory stimulators, and one or more computer processors, the one or more computer processors configured by computer readable instructions to execute computer program modules, the computer program modules comprising a sensory stimulus module, a slow wave sleep module, a timing module, and a control module, the method comprising:
   obtaining sensory stimulus parameters with the sensory stimulus module that define a prompt sensory stimulus to be provided to the subject, the prompt sensory stimulus comprising a first type of sensory stimulus, the first type of sensory stimulus configured to recreate a learning context corresponding to a period of wakeful learning by the subject;
   controlling the one or more slow wave sleep inducers with the slow wave sleep module to induce slow wave sleep in the subject by providing a second type of sensory stimulus to the subject, the second type of sensory stimulus being different than the first type of sensory stimulus such that the second type of sensory stimulus does not recreate the learning context corresponding to the period of wakeful learning by the subject;
   determining a timing with respect to the control of the one or more slow wave sleep inducers for delivery of the prompt sensory stimulus with the timing module such that the prompt sensory stimulus will be provided to the subject during induced slow wave sleep; and
   controlling the one or more sensory stimulators with the control module to, responsive to the slow wave sleep being induced, provide the prompt sensory stimulus to the subject according to the obtained sensory stimulus parameters at the determined timing;
   wherein the timing for delivery of the prompt sensory stimulus is determined such that delivery of the prompt sensory stimulus begins a predetermined amount of time after the start of slow wave sleep induction.

9. The method of claim 8, further comprising generating output signals with one or more sensors conveying information related to a current sleep stage of the subject.

10. The method of claim 9, further comprising identifying non-rapid eye movement (NREM) sleep in the subject based on the output signals; and
   determining, with the timing module, the timing for delivery of the prompt sensory stimulus based on identification of NREM sleep in the subject.

11. The method of claim 8, further comprising obtaining, with the sensory stimulus module, the sensory stimulus parameters that define the prompt sensory stimulus based on a wakeful sensory stimulus provided to the subject during the period of wakeful learning by the subject.

12. The method of claim 11, further comprising controlling, with the control module, the one or more sensory stimulators to provide the prompt sensory stimulus to the subject such that the prompt sensory stimulus corresponds to the wakeful sensory stimulus provided during the period of wakeful learning.

13. The method of claim of claim 11, wherein the sensory stimulus parameters that define the prompt sensory stimulus include the first type of sensory stimulus, a duration, an intensity, a frequency, and a duty cycle of the prompt sensory stimulus.

14. The method of claim 8, wherein the predetermined amount of time after the start of slow wave sleep induction is determined based on a typical amount of time between the start of slow wave sleep induction and the start of slow wave sleep in the subject.

15. A system for enhancing knowledge consolidation in a subject during sleep; the system comprising:
 means for inducing slow wave sleep in the subject;
 means for providing sensory stimuli to the subject;
 means for obtaining sensory stimulus parameters that define a prompt sensory stimulus to be provided to the subject, the prompt sensory stimulus comprising a first type of sensory stimulus, the first type of sensory stimulus configured to recreate a learning context corresponding to a period of wakeful learning by the subject;
 means for controlling the means for inducing slow wave sleep in the subject to induce slow wave sleep in the subject by providing a second type of sensory stimulus to the subject, the second type of sensory stimulus being different than the first type of sensory stimulus such that the second type of sensory stimulus does not recreate the learning context corresponding to the period of wakeful learning by the subject;
 means for determining a timing with respect to the control of the one or more slow wave sleep inducers for delivery of the prompt sensory stimulus such that the prompt sensory stimulus will be provided to the subject during induced slow wave sleep;
 means for controlling the means for providing sensory stimuli to, responsive to the slow wave sleep being induced, provide the prompt sensory stimulus to the subject according to the obtained sensory stimulus parameters at the determined timing; and
 means for determining the timing for delivery of the prompt sensory stimulus such that delivery of the prompt sensory stimulus begins a predetermined amount of time after the start of slow wave sleep induction.

16. The system of claim 15, further comprising means for generating output signals conveying information related to a current sleep stage of the subject.

17. The system of claim 16, further comprising means for identifying non-rapid eye movement (NREM) sleep in the subject based on the output signals; and
 wherein the means for determining a timing is further configured to determine the timing for delivery of the prompt sensory stimulus based on identification of NREM sleep in the subject.

18. The system of claim 15, wherein the means for obtaining sensory stimulus parameters is further configured to obtain the sensory stimulus parameters that define the prompt sensory stimulus based on a wakeful sensory stimulus provided to the subject during the period of wakeful learning by the subject.

19. The system of claim 18, wherein the means for controlling the means for providing sensory stimuli is further configured to control the means for providing sensory stimuli to provide the prompt sensory stimulus to the subject such that the prompt sensory stimulus corresponds to the wakeful sensory stimulus provided during the period of wakeful learning.

20. The system of claim of claim 18, wherein the sensory stimulus parameters that define the prompt sensory stimulus include the first type of sensory stimulus, a duration, an intensity, a frequency, and a duty cycle of the prompt sensory stimulus.

21. The system of claim 15, wherein the predetermined amount of time after the start of slow wave sleep induction is determined based on a typical amount of time between the start of slow wave sleep induction and the start of slow wave sleep in the subject.

* * * * *